(12) United States Patent  
Hao et al.

(10) Patent No.: US 8,684,933 B2  
(45) Date of Patent: Apr. 1, 2014

(54) HANDHELD ULTRASOUND COLOR FLOW IMAGING SYSTEM WITH MECHANICALLY SCANNED, MECHANICALLY FOCUSED MULTI-ELEMENT TRANSDUCERS

(75) Inventors: Xiaohui Hao, Blaine, WA (US); Donald J. Nisler, Snohomish, WA (US)

(73) Assignee: ImSonic Medical, Inc., Blaine, WA (US)

( * ) Notice: Subject to any disclaimer, the term of this patent is extended or adjusted under 35 U.S.C. 154(b) by 754 days.

(21) Appl. No.: 12/858,117

(22) Filed: Aug. 17, 2010

(65) Prior Publication Data

US 2012/0046548 A1    Feb. 23, 2012

(51) Int. Cl.
*A61B 8/06* (2006.01)
*A61B 8/14* (2006.01)
*G01F 1/66* (2006.01)

(52) U.S. Cl.
USPC .................. 600/441; 600/457; 73/861.25

(58) Field of Classification Search
None
See application file for complete search history.

(56) References Cited

U.S. PATENT DOCUMENTS

| | | | |
|---|---|---|---|
| 4,155,259 A | 5/1979 | Engeler | |
| 4,398,539 A | 8/1983 | Proudian | |
| 5,291,892 A * | 3/1994 | O'Donnell | 600/454 |
| 5,363,851 A | 11/1994 | Hall | |
| 5,680,865 A | 10/1997 | Tanaka | |
| 5,690,110 A | 11/1997 | Tanaka | |
| 5,738,098 A * | 4/1998 | Brock-Fisher et al. | 600/472 |
| 5,876,341 A * | 3/1999 | Wang et al. | 600/441 |
| 6,057,632 A * | 5/2000 | Ustuner | 310/334 |
| 6,106,472 A * | 8/2000 | Chiang et al. | 600/447 |
| 6,110,119 A * | 8/2000 | Hall | 600/455 |
| 6,120,454 A * | 9/2000 | Suorsa et al. | 600/466 |
| 6,123,672 A * | 9/2000 | Miller et al. | 600/455 |
| 6,540,682 B1 * | 4/2003 | Leavitt et al. | 600/447 |
| 7,431,698 B2 * | 10/2008 | Bruestle | 600/459 |
| 8,038,619 B2 * | 10/2011 | Steinbacher | 600/444 |
| 8,475,380 B2 * | 7/2013 | Kristoffersen et al. | 600/443 |
| 2002/0139193 A1 | 10/2002 | Angelsen | |
| 2003/0125629 A1 | 7/2003 | Ustuner | |
| 2004/0158154 A1 | 8/2004 | Hanafy | |
| 2005/0113689 A1 * | 5/2005 | Gritzky | 600/437 |
| 2005/0197572 A1 | 9/2005 | Williams | |
| 2007/0016044 A1 * | 1/2007 | Blalock et al. | 600/443 |
| 2009/0012401 A1 | 1/2009 | Steinbacher | |
| 2010/0056912 A1 * | 3/2010 | Urness et al. | 600/437 |
| 2010/0324418 A1 * | 12/2010 | El-Aklouk et al. | 600/441 |

* cited by examiner

*Primary Examiner* — Long V. Le
*Assistant Examiner* — Angela M Hoffa
(74) *Attorney, Agent, or Firm* — Christensen O'Connor Johnson Kindness PLLC

(57) ABSTRACT

A portable ultrasound imaging system employs a mechanically focused multi-element circular annular transducer that is mechanically scanned using a motor. Received echoes are processed to form two dimensional gray scale B mode images or two dimensional color tissue flow images which are displayed on a display unit. In case of color flow imaging, a high pulse repetition frequency imaging sequence is employed for a reasonable frame rate and special down-sampling techniques are applied to achieve an effective low pulse repetition frequency for flow estimation with enough signal to noise ratio. The system also includes a docking subsystem which charges a system battery and transfers patient and image data between a PACS system, workstation or other information system and the portable ultrasound imaging system.

17 Claims, 12 Drawing Sheets

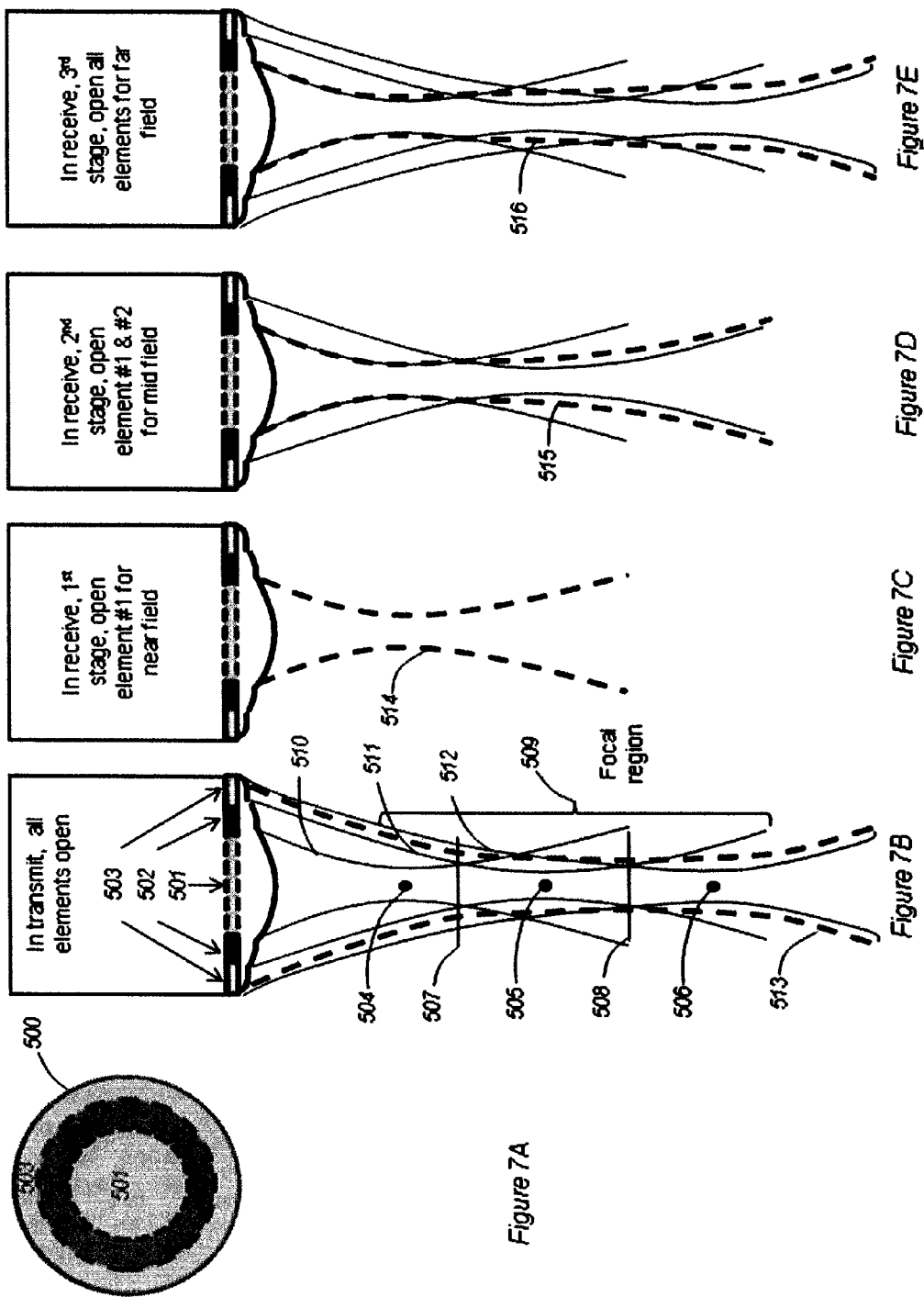

HANDHELD ULTRASOUND COLOR FLOW IMAGING SYSTEM WITH MECHANICALLY SCANNED, MECHANICALLY FOCUSED MULTI-ELEMENT TRANSDUCERS

BACKGROUND

In recent years, portable handheld ultrasound imaging systems such as the ones described in U.S. Pat. No. 6,540,682 and U.S. Pat. No. 6,106,472 have been widely adopted in medical healthcare markets, especially point-of-care markets such as Emergency Medicine, Fertility, Surgery, and Anesthesia. However, due to the complexity of ultrasound imaging systems and the associated phase array transducers, manufacturing of these systems and transducers is very costly, resulting in expensive portable ultrasound systems. The high price limits the use of portable ultrasound imaging systems by many healthcare providers, and prevents them from becoming an imaging 'stethoscope', even though advanced technology allows a handheld ultrasound imaging system to be used at the point-of-care. A less complex, low cost handheld ultrasound imaging system will allow an ultrasound imaging system to become the imaging 'stethoscope' and become a basic tool in every area of the healthcare system. A mechanically focused single element imaging system may be a solution since no complex phased array and corresponding beamforming system are necessary. However, a single element imaging system limits the image detail resolution, and the use of a driving motor for scanning makes color flow imaging very difficult to implement in the conventional way. This invention provides solutions for the image resolution and color flow imaging issues associated with ultrasound imaging systems with mechanically focused and motor driven transducers.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

This invention presents a portable and configurable ultrasound imaging system which is integrated with a variety of mechanically scanned, mechanically focused circular annular multi-element transducers, and supports a variety of imaging scan sequence and processing techniques. In particular, this portable ultrasound imaging system provides color flow imaging sequence and corresponding processing methods. The transducer integrates an acoustic scan head and a mechanical driving system. The acoustic scan head is a multi-element circular annular array. These elements are arranged to mechanically focus an ultrasound beam at different depths. The mechanical focus is achieved by using different lenses for different elements, or by applying a different acoustic stack curvature for each element. No beamforming phase delays are required for the individual elements to focus both the transmit signal and receive echoes. Correspondingly, beamforming circuitry is not necessary in the system. For the mechanical driving system, typically, a standard stepping motor or linear stepping motor is mounted inside the transducer assembly. Either through a mechanical transmission subsystem or directly, the stepping motor drives the acoustic scan head to move inside the transducer either in a rotational manner or in a sliding manner to form a fan shape or rectangular acoustic scan field. A motor controller controls the movement of the stepping motor based on system imaging sequences such as B mode or Color Flow mode imaging sequences. The ultrasound imaging system can further turn different transducer elements on or off during transmit and/or receive to apply a different mechanical focus at different depths such that a narrow receive beam can be achieved. The imaging system processes the received echo directly to form an image, or it extracts color flow information if color flow imaging sequence is applied.

For color flow imaging, instead of interleaving ensemble beams in an imaging sequence, this system fires a full set of color ensemble beams in a high pulse repetition frequency (PRF) at each beam position before it moves to another beam position. In color flow processing, two mechanisms can be employed. In one mechanism, the high PRF color ensemble set is down sampled into several subgroups so that each has less ensemble beams at a lower PRF. Color information is extracted from each subgroup and then averaged to improve the flow signal to noise ratio (SNR). In another mechanism, multi-path flow processing is employed where one path processes the lower PRF ensembles and the other path processes the original high PRF color ensembles directly. The results from two paths are combined to satisfy both non-aliasing and low flow sensitivity requirements. The processing is done by a configurable processor in the imaging system. The portable and reconfigurable system allows alternative imaging applications and operating modes. The processing algorithms and operating features are reconfigurable through software updates. This invention further includes a multi-functional intelligent dock for the portable ultrasound imaging system. The multi-functional intelligent dock is used for battery charging, study data transfer, patient management, PACS system communication, and other functions.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 7A-7E give an illustration of dynamic focus through element control with a three-element circular annular array scan head where each element is mechanically focused using different lenses at different depths.

DETAILED DESCRIPTION

Figure 1:
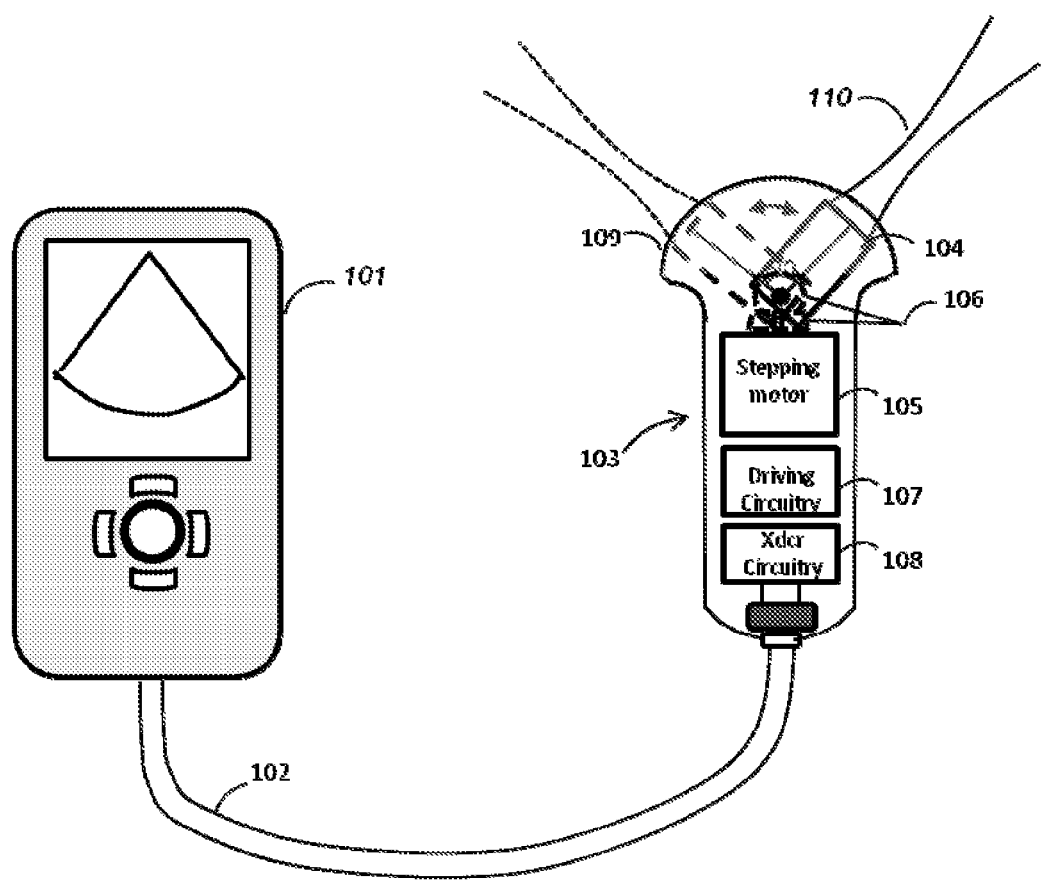
FIG. 1 is a graphical view illustrating a portable handheld ultrasound imaging system with a multi-element circular annular transducer assembly that uses a mechanical focus and a mechanical scan.

FIG. 1 is a graphical view illustrating a portable handheld ultrasound imaging system 101 connected with a mechanically scanned, ultrasound transducer assembly 103 through interface cable 102 in accordance with the disclosed technology.

The transducer assembly 103 transmits acoustic energy into human tissue, receives the reflected echoes and transforms these echoes into electronic signals. The transformed electronic signals are sent to the handheld ultrasound processor 101 through interface cable 102. The handheld processor 101 processes the received electronic signals. After processing, a two-dimensional image generated from the received echo is displayed on a liquid crystal display, or other display technology incorporated with the ultrasound processor. Certain user controls are supplied and associated with the ultrasound processor to allow the user control of the imaging, or to perform further operations such as measurements. The processing of the received echo signals is configurable through software.

The transducer assembly 103 is detailed in FIG. 1. It includes an acoustic scan head 104, which is not a phase array, but rather a multi-element (e. g. <=8 elements) mechanically focused, circular annular ultrasound array. The scan head 104 is attached to a stepping motor 105 inside the transducer assembly through a mechanical transmission system 106. The mounting is done in a way that the rotation center is orthogonal and intersecting with the physical center line of the scan head and is located at the bottom part of the scan head. The motor driving circuitry 107 provides the motor 105 power and logic instructions for it to move. When motor 105 rotates, it moves scan head 104 through the mechanical transmission system 106. At each predefined location during a scan, the scan head 104 transmits signals to and receives signals from the tissue. The acoustic field envelope is shown as 110 in the figure. A full scan from one side to another side forms a fan-shaped acoustic scan region with an approximate 90 degree opening angle. An acoustic transparent shell 109 encloses the scan head. Inside the transducer, lubricant oil is used to provide lubrication for the movement of the scan head and provide acoustic paths for sound transmission. The transducer assembly also includes inductor tuning circuit 108.

Figure 2:
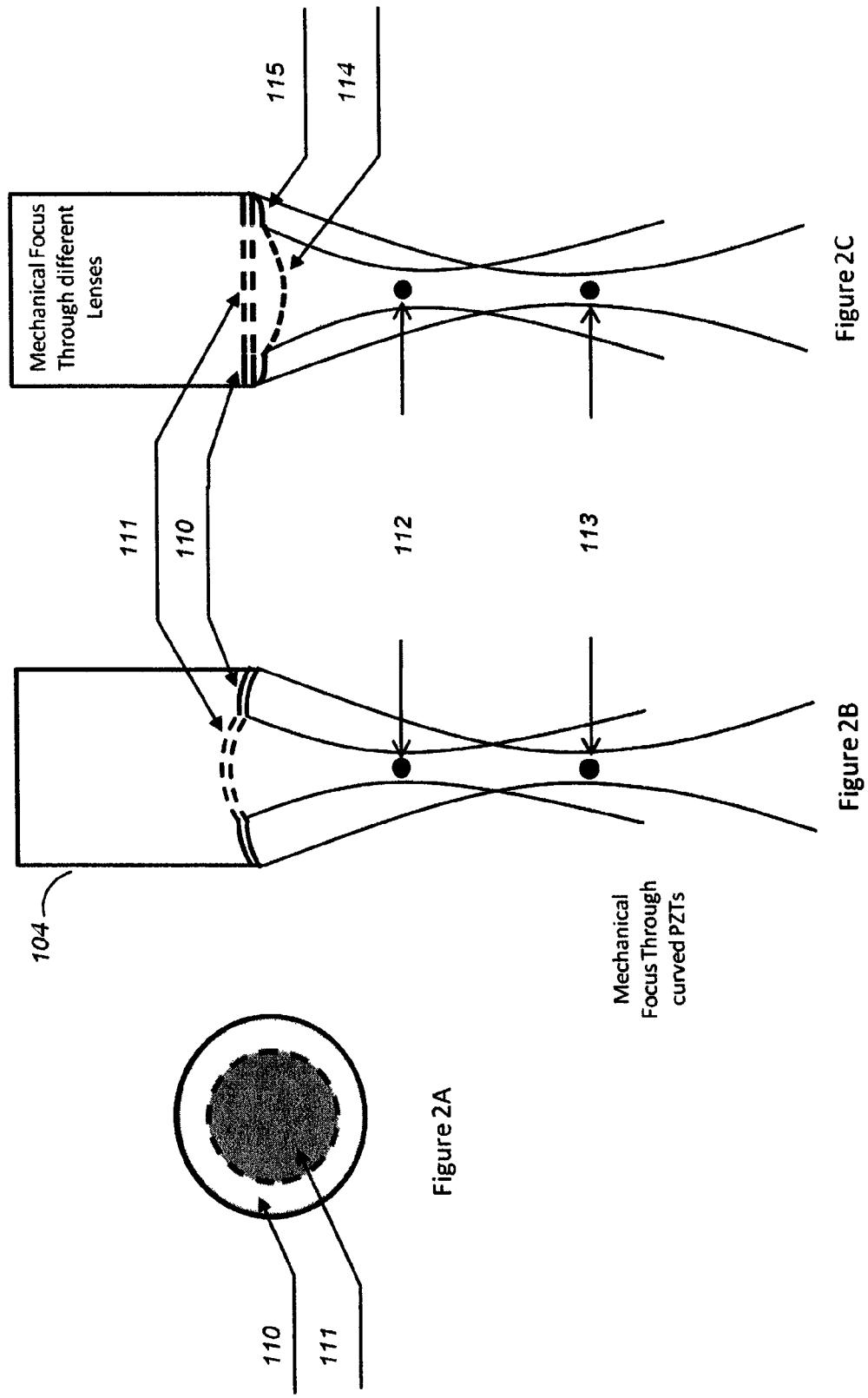
FIGS. 2A-2C illustrate a multi-element circular annular array scan head as part of a transducer assembly.

FIGS. 2A-2B illustrate an embodiment of a scan head 104 in the transducer assembly. The scan head 104 has two circular elements 110 and 111 as shown in FIG. 2A. The two elements are mechanically focused at different depths. FIGS. 2B and 2C illustrate two mechanical focusing schemes for this two-element circular transducer. In FIG. 2B, the mechanical focus is achieved by shaping the piezoelectric acoustic stacks 110 and 111. As can be seen, the inner circular element or disc 111 is shaped with a radius of curvature equal to the focal depth from the disk surface center to focal point 112, and the outside annular element 110 has a larger radius of curvature to form a focal point at point 113. In FIG. 2C, the two circular elements 110 and 111 have flat piezoelectric acoustic stacks, whose mechanical focus is achieved by using a lens with a different shape and thickness. The center lens 114 is thicker to form a focal point at point 112 for the inner circular element 111 and the outside annular lens 115 is thinner in annular shape to form a focal point at point 113 for the outside annular circular element 110. Both focal points 112 and 113 are closer to the transducer surface compared to the natural focal points decided by the diameters of the two flat transducer elements.

The scan head 104 can have more than two circular elements with each element focused at a different depth to form a long focal region. Focusing is achieved mechanically, either by using different lenses, by shaping the piezoelectric stacks to focus at the desired point, or by letting the focus be the natural focus of the flat elements.

The multi-element circular annular acoustic scan transducer can be made using several materials or combinations of material. For example, it can be made by using piezo-ceramics or piezo-single crystal (PMN-PT, PIN-PT) materials, thick films of piezo-ceramics, piezo-single crystal (PMN-PT, PIN-PT) materials, or it can be made by using 1-3 composites of piezo-ceramics or piezo-single crystal (PMN-PT, PIN-PT) materials. The 1-3 composites materials may consist of regular post structures, such as squares post, triangular post or random structures. Furthermore, the multi-element circular annular ultrasound transducer can be made using cMUT transducers which are basically silicon chips.

Beyond the mechanical rotation scheme illustrated in FIG. 1, the scan head can also move along a curved or linear rail driven by the stepping motor or a linear motor to form a sector scan, or a rectangular region scan as detailed in the following sections.

Figure 3:
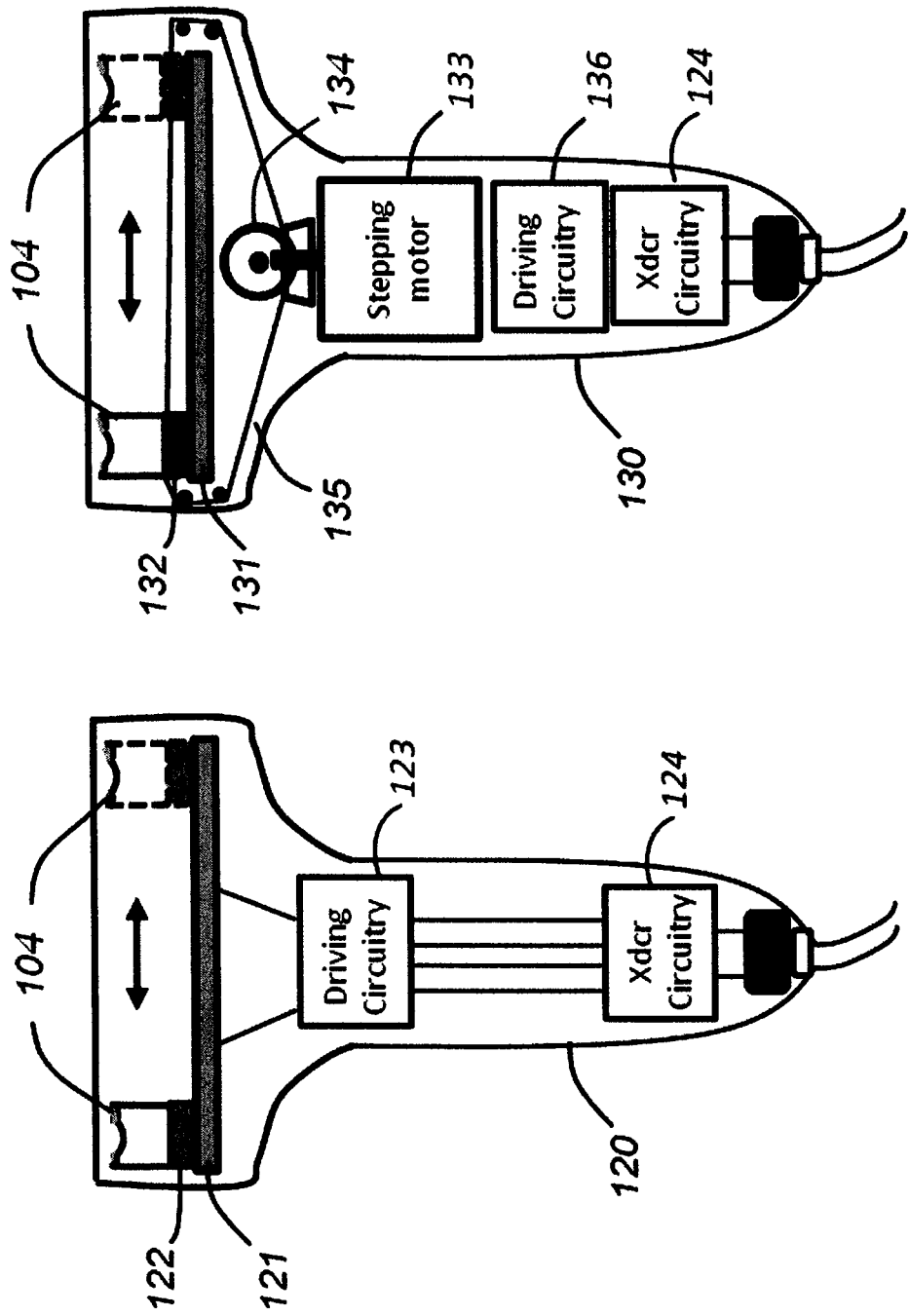
FIG. 3 illustrates two mechanical transmission schemes for a rectangular shaped scan transducer assembly.

FIG. 3 illustrates two mechanical transmission schemes for a rectangular shaped scan transducer assembly. In transducer assembly 120, a linear motor, a linear ultrasonic motor, or a linear stepping motor is used. Acoustic scan head 104 is mounted on a moving part 122 of the motor that moves back and forth along the linear rail 121, which serves as the fixed part of the motor with coils inside. The scan head 104 may stop at predefined locations and send pulses into the tissue and receive the reflected echoes. When the scan head has finished a move from one end to the other end, a rectangular region scan can be formed. In an alternative embodiment, the transducer assembly 130, the scan head 104 is attached to moving cart 132, which is connected with the motor 133 using a pulling string 135 through mechanical transmission set 134. When the motor 133 rotates, it pulls the string 135 in either direction according to its rotation direction, which moves the cart 132 along the linear rail 131 through transmission 134. This results in a linear motion of the scan head 104 along the rail 131 and forms a rectangular shaped scan.

For either the linear motor driving scheme or stepping motor plus mechanical pulling subsystem scheme, a motor driving circuitry 123 or 136 is mounted inside the probe assembly to drive the linear motor or the regular stepping motor. Both assembly 120 and 130 include the regular transducer tuning circuitry 124, which compensates for the capacitance of the transducer elements with inductance.

Figure 4:
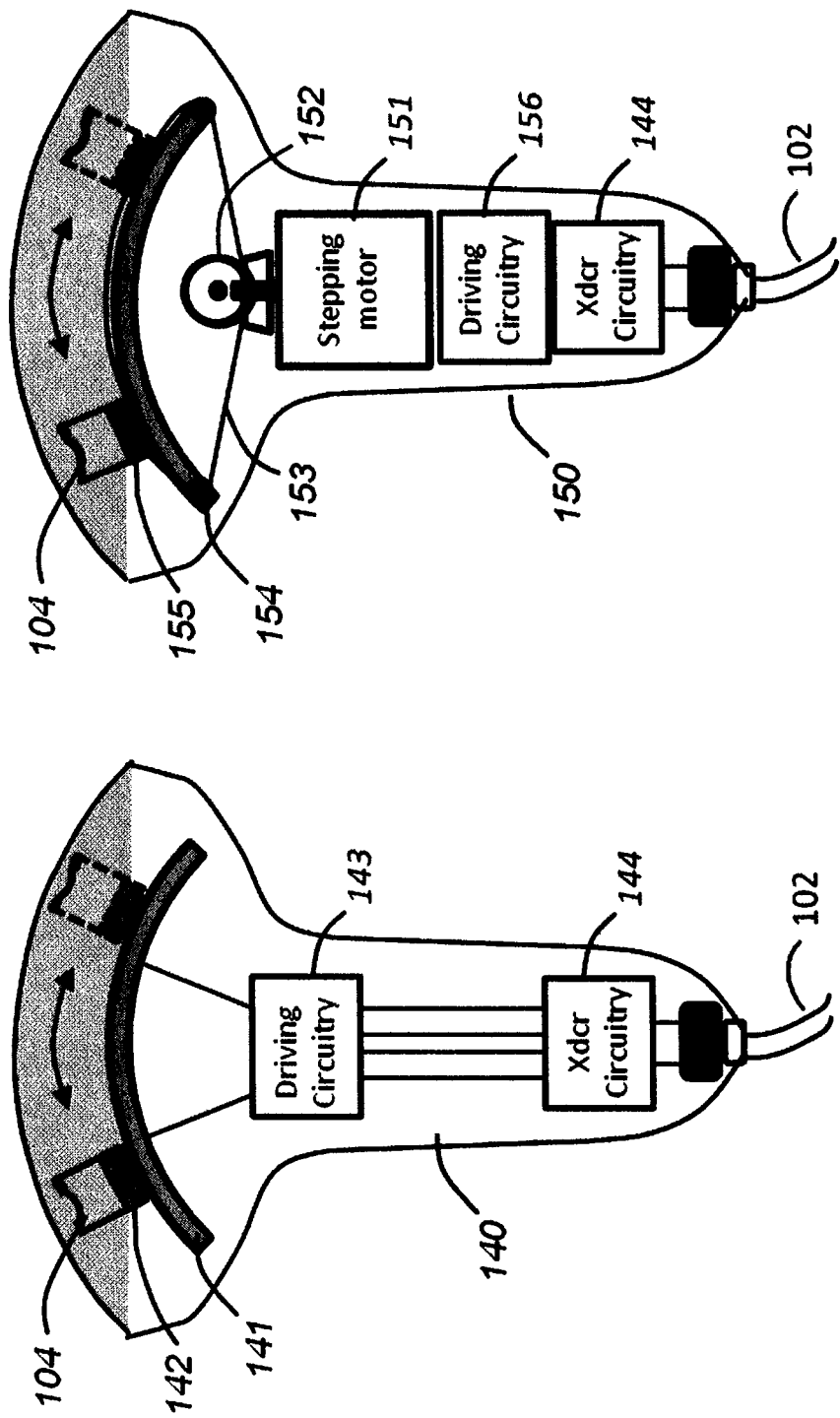
FIG. 4 illustrates a fan shaped scan transducer assembly.

FIG. 4 illustrates two fan-shaped scan transducer assemblies. In this illustration, a curve linear rail is used to guide the motion of the scan head. In one implementation as shown in assembly 140, a curve linear motor is employed. A rail 141 serves as the fixed part of the motor with coils inside and a moving part 142 is assembled on top of the rail. A motor driving circuitry 143 drives the moving part 142 to move along the rail 141 from the left end to the right end or vice versa. The moving part 142 moves the scan head 104 which is mounted on top of it. The scan head 104 sends acoustic pulses to and receives echo signals from the tissue while moving and a fan-shaped scan region is formed. In another implementation scheme as shown in transducer assembly 150, a regular stepping motor 151 moves the scan head 104 that is mounted on a moving cart 155 along a curve linear rail 154 through a mechanical transmission set 152 using pulling string 153 attached to the moving cart 155. A motor driving circuit 156 drives the stepping motor. When the motor 151 rotates, it pulls the string 153 in a desired direction, which then moves cart 155 along the curve linear rail. Correspondingly, this moves the scan head 104 along the curve linear rail.

For both transducer assemblies 140 and 150, transducer circuitry 144 is used for compensating the capacitance of the transducer elements before sending the signal back to the imaging system through interface cable 102.

For the above-described transducer assemblies, lubricant oil is used to fill the transducer head for smooth movement, either rotating or sliding along a curved or linear rail. The lubricant oil also serves as an acoustic path for the sound wave propagation.

Figure 5:
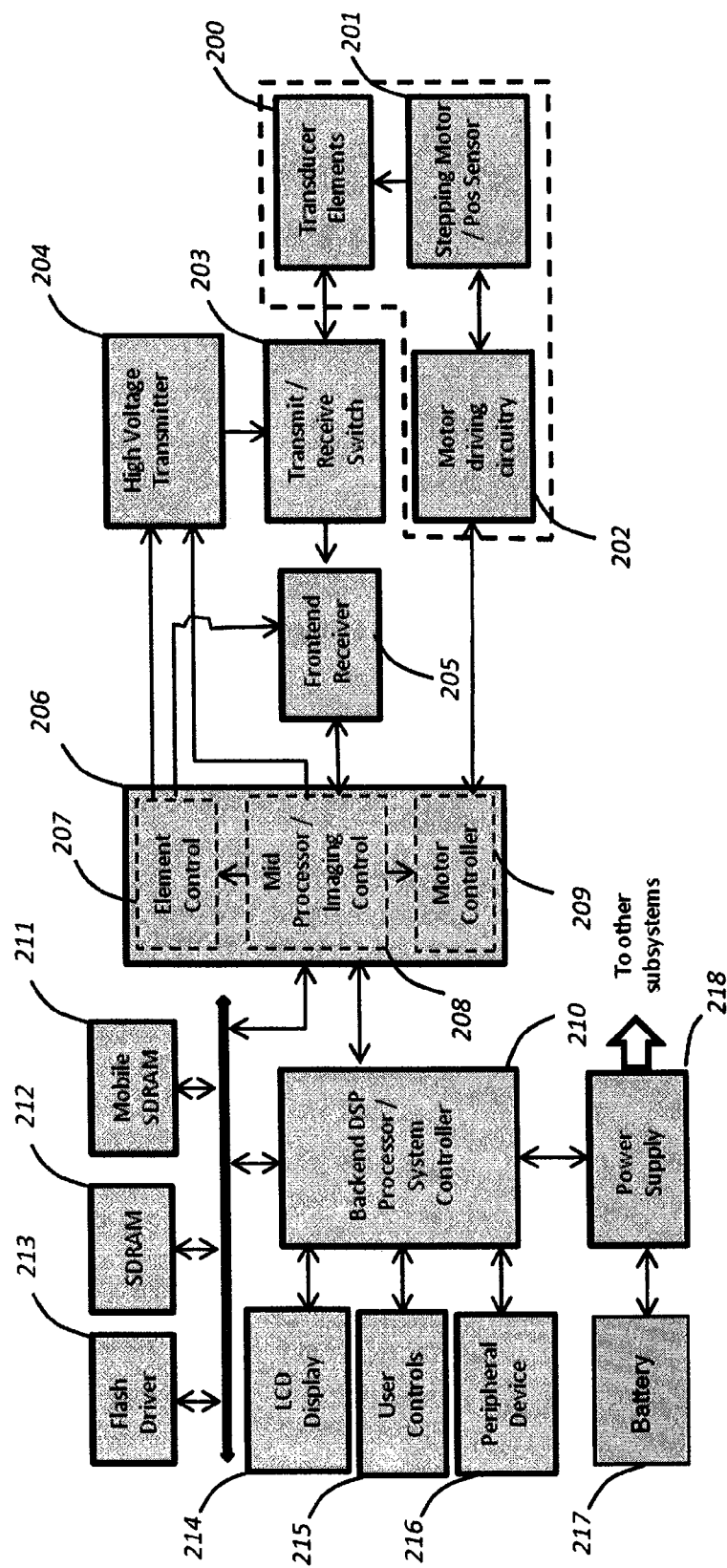
FIG. 5 is a configuration block diagram of one embodiment of the handheld imaging system.

A block diagram of the handheld imaging system 101 connected to the transducer assembly 103 shown in FIG. 1 is illustrated in FIG. 5.

The system sends signals to and receives signals from the transducer elements 200 through the transmit/receive (T/R) switch 203. A high voltage transmitter 204 takes the logic pulse and transmit timing control signal, generates a high voltage pulse (+/−30 Volts to +/−100 volts) and sends the pulse to T/R switch 203 when transmit is enabled. The T/R switch 203 passes high voltage (>60 volts in peak to peak value) pulses to the transducer elements 200 during transmit. It also prevents the high transmit voltage from being applied to the front-end receiver 205 which can tolerate no more than 2~4 volts peak to peak input. During receive, the T/R switch 203 passes the weak electrical signals transformed from the received echoes by the transducer elements 200 to the front-end receiver 205.

Figure 6:
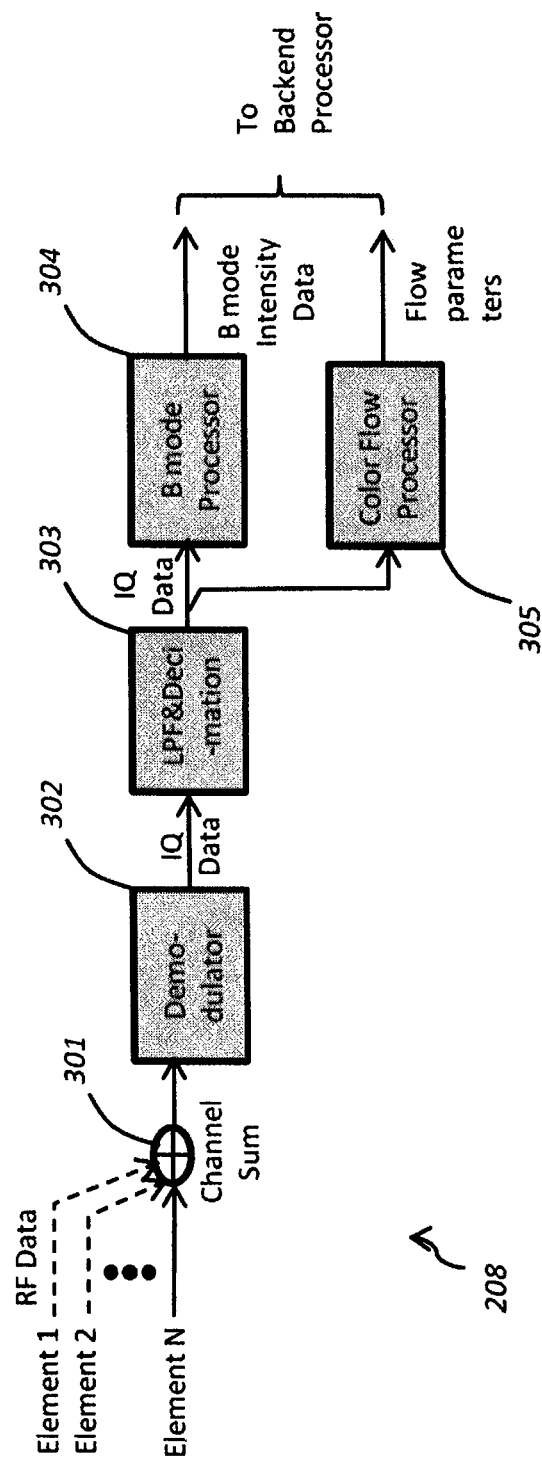
FIG. 6 is a configuration block diagram of signal processing in a Mid-Processor.

The front-end receiver 205 includes a number of integrated units each of which has several channels of low noise amplifiers (LNA), programmable gain amplifiers (PGA), and analog to digital converters (A/D). It amplifies the received echo signals, applies time-gain control to compensate both for depth dependent attenuation and focus gain. Focus gain can be compensated at this point because the received beam is already focused through the mechanical transducer. After time-gain compensation, the analog signal is converted into digital Radio Frequency (RF) data, and the converted RF data is sent to the mid-processor 206 for further processing. The mid-processor 206 handles both signal processing and imaging control, it includes three units: the mid processor and imaging control unit 208, the transducer element control unit 207, and the motor controller 209. These functions may be implemented in large scale FPGAs or an ASIC chip. Imaging control unit 208 processes the received RF data to form B-mode or color flow images. FIG. 6 shows an example diagram of mid processing performed in unit 208.

In this example shown in FIG. 6, the incoming RF data from different transducer elements through different channels are summed together at channel sum 301. As described above, there is no phase delay applied to each channel's RF data for digital beamforming since the received beams from all transducer elements are mechanically focused at predetermined focal depths. The summed RF data are sent to a demodulator 302, where RF data are shifted to base band In-phase and Quadrature (IQ) data. The IQ data is then low pass filtered and decimated in 303. In the B-mode case, the down sampled IQ data is sent to 304 for B-mode processing, where envelop detection and log compression are applied. In the case of Color Flow imaging, the decimated IQ data for color flow imaging is sent to color flow processor 305 where flow processing such as wall filtering, autocorrelation, flow parameter estimation, and thresholding are applied. After those steps, the flow parameters will be sent to backend processor 210 for further processing and display.

In FIG. 5, beyond the mid-processing for B-mode and Color flow imaging, imaging control unit 208 also controls imaging sequence. It controls the exact timing for transmit and receive and defines the exact spatial position of each beam. The beam position is modified by mechanically moving the multi-element circular transducer. The movement can be a rotation around a fixed axis as shown in FIG. 1, or linear sliding movement along a curve linear or linear rail as shown in FIG. 3 and FIG. 4. The imaging control unit 208 sends the beam position information to motor controller 209, which sets motor motion for each frame. The information generated by motor controller 209 is sent to motor driving circuitry 202, which translates this control logic into electronic control current to control the stepping or linear motor 201 inside the transducer assembly. The motor driving circuitry may be built inside or outside the transducer assembly 103. The motor unit 201 then moves the attached acoustic elements 200.

Element control unit 207 is used to achieve dynamic focus in the received signal to form a thin receive beam as described below.

FIGS. 7A-7E demonstrate the dynamic focus control methodology with a three-element circular array scan head 500 where each element is mechanically focused using different lenses at different depths. FIG. 7A is the front view of the scan head. There are three elements, an inner circular element 501, focusing at the shallowest focal point 504, a middle annular element 502, focusing at focal point 505, a depth deeper than focal point 504, and an outer annular element 503, focusing at the deepest focal point 506. The −3 dB intensity envelope for each element is shown in FIG. 7B. The −3 dB intensity envelope 510 of element 501 intersects with the −3 dB intensity envelope 511 of element 502 at depth d1 507, and the −3 dB intensity envelope 511 of element 502 intersects with the −3 dB intensity envelope 512 of element 503 at depth d2 508. From these intensity envelopes, it can be seen that if all elements are turned on at any time during receive, the resulting image will have reasonable lateral resolution in focal region 509, while, in near and far field, especially near field, the lateral resolution will be poor as shown by the −3 dB combined intensity envelope defined by dashed lines 513 in FIG. 7B.

To achieve good lateral resolution beyond just the focal region, the element control unit 207 in FIG. 5 turns on a different number of elements, or it will turn on different elements at different depths during receive and transmit. As an example, during transmit, all elements are turned on to deliver enough energy into tissue. During receive, the element control unit 207 first turns on element 501 for a thin beam in the near field as illustrated in FIG. 7C. When signals reflected from tissue in depths deeper than d1 507 (mid field) reach the probe surface, the element control unit 207 turns on element 502 so both element 501 and element 502 receive the reflected echo as shown in FIG. 7D. When signals reflected from tissue in depths deeper than d2 508 (far field) reach the probe surface, the element control unit 207 turns on all three elements 501, 502 and 503 to receive the reflected echo as shown in FIG. 7E. The −3 dB intensity envelopes 514, 515, 516 of the resulting beam at different stages are shown in FIGS. 7C, 7D and 7E by dash lines, respectively. From FIG. 7E, it can be seen that the final receive beam envelop 516 has a relatively uniform and thin shape in the lateral direction. Each time the element control unit 207 turns on a new element, the receive signal gain characteristics change. The element control unit 207 then modifies the time gain compensation curve correspondingly.

After mid-signal processing, the processed B-mode or Color Flow data are sent to the backend DSP processor 210. A large capacity SDRAM 212 is connected to the backend DSP processor 210 through the bi-directional data bus. Image data received is first sent to a large cine memory allocated in the SDRAM 212. Then it is read out by the backend DSP processor 210 for backend signal processing including edge enhancement, scan conversion, and tissue flow combination (in case of color flow imaging) to form a final two dimensional image. The image is then sent to the LCD 214 for display.

The backend DSP processor 210 also serves as the system controller with an embedded micro-processor. It runs a mobile operating system and takes care of system level control. First it manages all data transfer in DMA mode. This includes data transfer between flash driver 213, SDRAM 212 and mobile SDRAM 211, and data transfer between these memory devices and the mid processor 206 and the backend processor 210. Second, it handles all user controls. When a user operates the user controls 215, a user command is sent to the backend DSP processor 210 through a serial or dedicated peripheral bus. Backend DSP processor 210 analyzes the application and if an imaging control change is necessary, it stops the current imaging sequence, applies a new imaging sequence to all related subsystems such as the mid-processor 206, the mobile SDRAM 211, etc. After that, backend DSP processor 210 and imaging controller 206 start the new imaging sequence. Third, the backend DSP processor 210 manages peripheral devices 216. This may include a USB 2.0 interface, memory card, wireless card, or other devices. Fourth, the backend DSP processor 210 controls the interface and functions of power supply 218. The power supply 218 takes power from the battery 217, creates high voltages for transmitter 204, provides appropriate low voltage power supplies for all other subsystems, such as the motor 201, the front-end receiver 205, the backend processor 210, the mid-processor 206, the LCD display 214, the SDRAM 211, and all the peripheral devices 216. A smart power management scheme is applied to the power supply 218 to minimize power consumption with imaging on and off to save battery power. For example, when imaging is off, electronic components in transmitter 204, front-end receiver 205, motor driving circuitry 202, and others will be partially powered down to save power.

The system can easily be reconfigured to add additional imaging modes and imaging applications through software updates. The update software is written into the flash driver 213 then applied to the whole system. For example, imaging control sequence, mid-processing and backend processing can be modified to add Pulse Wave Doppler imaging and Continuous Wave Doppler imaging to provide the user additional information about blood flow. After the system is powered up, it will load the new software and send the new controls to the corresponding subsystems and apply the new imaging algorithms.

This imaging system can be used for Abdomen, Renal, OB/GYN, Small Parts and Cardiac ultrasound applications by selecting one of the three different types of transducers illustrated in FIG. 1, FIG. 3 and FIG. 4. For each application, corresponding system and imaging control software will be loaded.

In this portable ultrasound imaging system, the multi-element circular annular array transducer can also be changed to a single element circular transducer. In this case, the element control 207 will always turn on the same element in transmit and receive. All other processing and imaging sequences are unchanged.

Figure 8B:
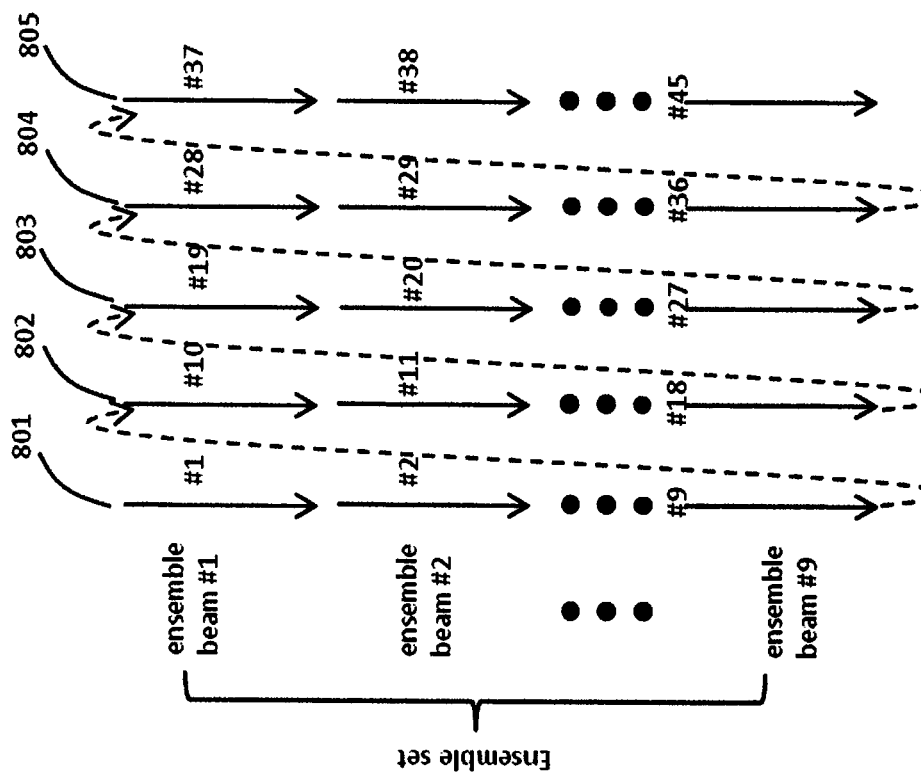
FIG. 8A illustrates a conventional color flow interleaving imaging sequence and FIG. 8B illustrates proposed color flow imaging sequence for the handheld imaging system with a mechanical scanned transducer in accordance with an embodiment of the disclosed technology.
Figure 8A:
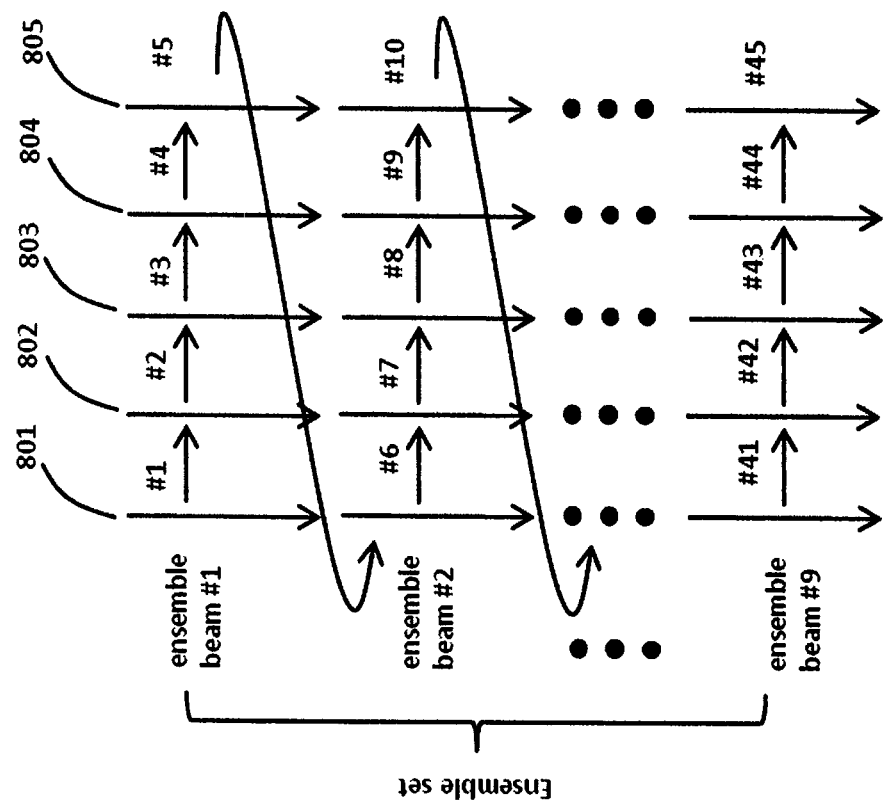

Due to the difficulty of the imaging sequence and beam position control, Color Flow imaging in ultrasound systems with a mechanically scanned transducer has not been attempted in a real application before. As an example, in abdomen imaging application, low velocity flow in liver and kidney tissue requires low Pulse Repetition Frequency (PRF) for Color Flow firings at the same beam position, typically, around 1 KHz or less. Here, color flow firings at the same beam position under a predetermined PRF are defined as one ensemble set, and each firing corresponds to one ensemble beam. Given a typical ensemble set size, e.g. 9, for abdomen applications, about 9 ms is needed to finish collecting enough flow information at one beam position. Generally, around 50 beam positions are used for the Color Flow region of interest. If the system always finishes all firings for one ensemble set at one beam position before move to another beam position, it will take 450 ms to finish the whole region of interest. This results in a super slow frame rate (FR) FR≈2 Hz, which is not acceptable in a real world application. If higher PRF, such as 5 KHz is used to improve the frame rate to a reasonable rate, e.g., 10 Hz, the low flow sensitivity will be dropped and most of the time, cannot be detected. The current state of art solves this issue by interleaving the imaging beams as shown in FIG. 8A and described below.

The system fires a beam, beam #1 as the first ensemble beam at beam position 801, assume a depth of 16 cm, it takes only about 0.2 ms. In order to achieve a 1 KHz PRF, the system can't fire another beam immediately at beam position 801. Instead, the system moves to beam position 802 and fires another beam, beam #2 for another 0.2 ms. Beam #2 is also the first ensemble beam at beam position 802. The system then continues to move to beam position 803, beam position 804, beam position 805, and at each position fires the first ensemble ultrasound beam at that position. After finish firing beam #5 at beam position 805, the system moves back to beam position 801 and fires the $2^{nd}$ ensemble beam, beam #6 at beam position 801. The system then moves to beam position 802 and fires the $2^{nd}$ ensemble beam, beam #7 then moves to position 803 and so forth. This process repeats until the system finishes firing the 9th ensemble beam, beam #45 at beam position 805. Assume there are 50 beam sets in the color flow imaging region of interest, the resulted FR is about 10 Hz, which is 5 times of 2 Hz and is more reasonable for abdomen imaging application. This mechanism is easy to implement with an electronically focused phased array imaging system by applying different time delays and turning on or off different elements. However, for an imaging system with mechanically scanned transducer, this is extremely difficult.

Under the above imaging conditions, 5 beam interleaving is not possible since it takes quite amount of time for the motor to move the ultrasound scan head back from beam position 805 to beam position 801. To make it practical, instead of 5 interleaving beams, assume only 3 interleaving beams are used. The motor only moves the transducer scan head to beam position 803 from beam position 801. After that, the system has to control the motor to move the transducer head back to beam position 801. The motor needs to be first decelerated to stop the forward motion, and then accelerated in backward direction to reach a certain speed such that it can be back on beam position 801 1 ms after it starts from beam position 801. If the angle distance between neighbored beams is 0.9 degree and it takes 0.2 ms for the scan head to move from one beam position to another, then the forward angular speed ω=0.9*pi/180/0.0002, ω≈79 rad/sec. In order to move back to beam position 801 on time for 1 KHz PRF, it has now 0.4 ms to stop, restart and accelerate to a speed to move back. In one of the solutions, the acceleration and deceleration speed will be acc=2,160,000 rad/sec^2 in order to reach a 432 rad/sec angular speed in 0.2 ms to move back to beam position 801. For a transducer scan head shown in FIG. 1, with length 0.02 meter, mass 10 gram, and a 0.01 meter diameter, the inertia of the scan head when rotating from bottom is about In≈1.33e−6 kgm^2. Thus the power required to drive this motor can be calculated as: P=In*acc*ω≈222 W.

Consider the motor driving circuitry efficiency, at least 300 W is needed to supply to the motor and its driving circuitry to achieve a ~6 Hz frame rate. This makes it impossible to perform flow imaging in a mechanically scanned transducer in the scan direction since just the amount of heat generated in the transducer scan head from the dissipation of the energy passed from motor could burn the transducer immediately. If the system only moves the transducer scan head to beam position 802 then moves back, a smaller acceleration speed could be used. Still, at least 75 W is needed to drive the motor to move the scan head back and forth and this only gives a 4 Hz frame rate.

From above, it is clear that beam interleaving is not possible for an ultrasound system using a mechanically scanned transducer. In the mean time, a 2 Hz frame rate is not useful for real time ultrasound imaging.

In order to do Color Flow imaging with reasonable power consumption using a mechanically scanned transducer, this invention provides a practical, non-interleaving color flow imaging sequence and two associated processing methods. The imaging sequence is shown in FIG. 8B. In detail, after firing the first ensemble beam, beam #1 at beam position 801, instead of moving the transducer to next beam position 802 immediately, or waiting for 1 ms to fire another ensemble beam at position 801 to satisfy the 1 KHz low PRF requirement, the system fires the second ensemble beam, beam #2 at beam position 801 immediately. Given an example, 0.2 ms per beam, this results in a 5 KHz PRF. For each ensemble beam, an ultrasound pulse is delivered to the tissue and the received echo signals are sampled at a number of different depths, e.g. every 0.1 mm. After finishing 9 ensemble beams, basically, beams #1-#9 form one ensemble set, at beam position 801, the system will move to next beam position 802 and fire another ensemble set of beams, beam #10—beam #18 before it moves to next beam position. This process continues until the whole color flow region of interest is covered. In case of 50 beam positions as described above, a 10 Hz frame rate can be achieved.

Figure 9:
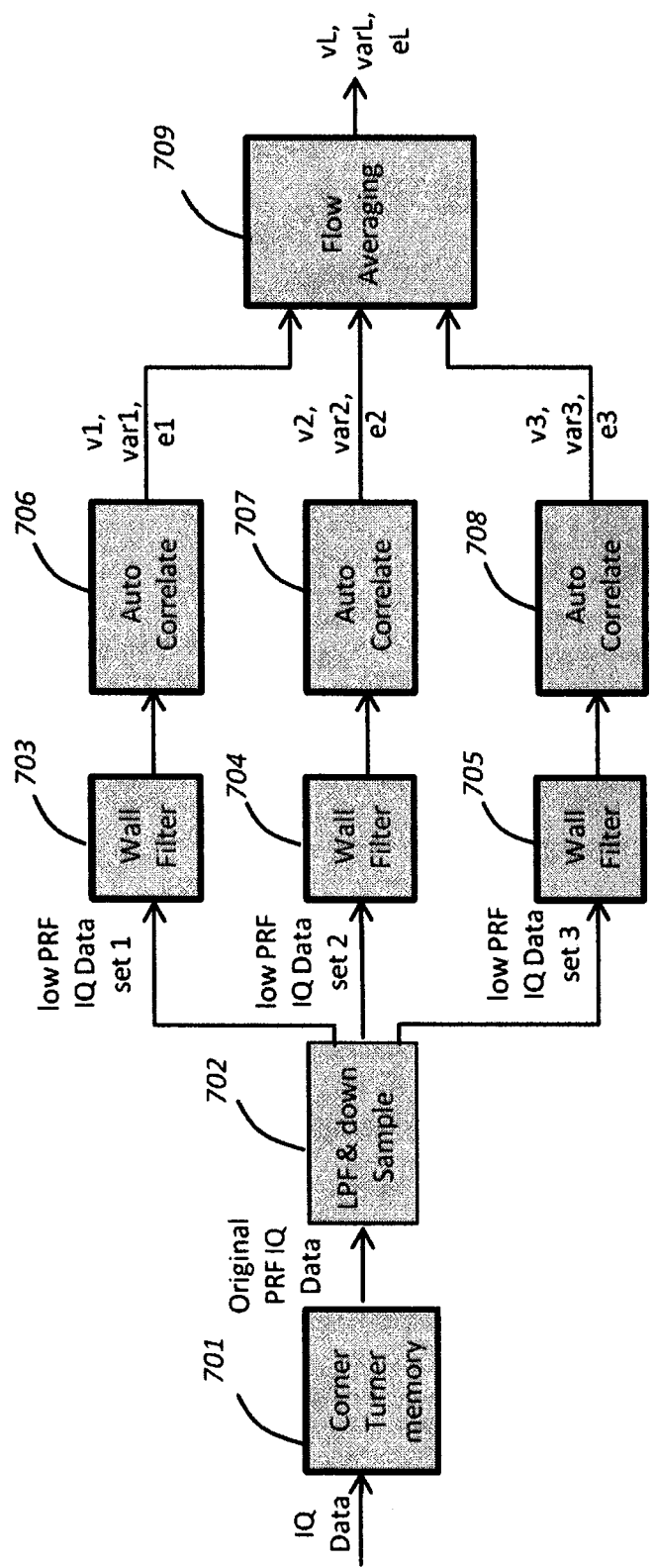
FIG. 9 is a configuration block diagram of one embodiment of the multi-subgroup down-sampled PRF color flow processing for a system with a mechanically scanned ultrasound transducer in accordance with an embodiment of the disclosed technology.

Method 1: With regular flow processing methods, a 5 KHz PRF will not satisfy the low flow sensitivity requirements in slow flow detection imaging applications such as Abdomen, Renal, and OB applications. A direct solution is to downsample the high PRF imaging data by a controllable decimation ratio. A careful selection of the decimation ratio can result in reasonable PRF for slow flow velocity estimation. The down side is that the ensemble size drops by a rate of decimation ratio, thus reducing the SNR. Typically, the flow estimation SNR is a function of $\sqrt{\text{ensembleSize}-1}$, thus, when the ensemble size drops from 9 to 3, the estimated flow SNR dropped by 6 dB. To solve this issue, this technology disclosed herein provides a processing method where the high PRF original data will be re-sampled to yield multiple groups of lower PRF data before regular color flow estimation is applied. An example is shown as 700 in FIG. 9. The IQ data collected from an ensemble set with full ensemble beams are sent to corner turner memory 701 where the data is first rearranged such that the IQ data, $I_i$, $Q_i$, i=1 to N, N is the ensemble size at the same depth, from different ensemble beams, at original PRF 5 KHz are put in the same column or row for easy access. The rearranged data are then taken out one ensemble set by one ensemble set for flow parameter estimation. As an example, one ensemble data set, at the original 5 KHz PRF, with ensemble size N=9, is represented by: $(I_1, Q_1)$, $(I_2, Q_2)$, $(I_3, Q_3)$, $(I_4, Q_4)$, $(I_5, Q_5)$, $(I_6, Q_6)$, $(I_7, Q_7)$, $(I_8, Q_8)$, $(I_9, Q_9)$. This data set is sent to preprocessor 702, where this full ensemble data is first low pass filtered with finite impulse response (FIR) filter, then reorganized to several new sub-groups based on a predetermined decimation ratio which is an integer number. The number of new sub-groups, L, equals the decimation ratio. In this example, with an ensemble size N=9, decimation ratio 3, the number of sub-group sets L equals 3 with each sub group set has a new ensemble size M, M=N/L=3. The three sets are: set 1, $(I_1, Q_1)$, $(I_4, Q_4)$, $(I_7, Q_7)$; set 2, $(I_2, Q_2)$, $(I_5, Q_5)$, $(I_8, Q_8)$; set 3, $(I_3, Q_3)$, $(I_6, Q_6)$, $(I_9, Q_9)$. It can be seen that each sub-group is a down sampled version of original ensemble data with a down sample rate of 3. They form the new ensemble data sets at PRF', where PRF'=PRF/(decimation ratio)=1.67 KHz as:

new set 1, $(I_1^{s1}, Q_1^{s1})=(I_1,Q_1)$, $(I_2^{s1},Q_2^{s1})=(I_4,Q_4)$, $(I_3^{s1}, Q_3^{s1})=(I_7,Q_7)$ new set 2, $(I_1^{s2}, Q_1^{s2})=(I_2,Q_2)$, $(I_2^{s2},Q_2^{s2})=(I_5,Q_5)$, $(I_3^{s2}, Q_3^{s2})=(I_8,Q_8)$ new set 3, $(I_1^{s3}, Q_1^{s3})=(I_3,Q_3)$, $(I_2^{s3},Q_2^{s3})=(I_6,Q_6)$, $(I_3^{s3}, Q_3^{s3})=(I_9,Q_9)$ Each of these three sets are sent to a corresponding wall filter, 703, 704, and 705 where a FIR or infinite impulse response (IIR) filter will be applied to remove the tissue clutter. The filtered data will then be passed to auto correlate functional blocks 706, 707, 708 simultaneously to estimate the flow information. The estimation is done using Kasai's technology as described below. First, the autocorrelation of new ensemble sets for 0 lag and 1 lag are acquired as below:

$$R(0) = \sum_{i=1}^{NewEnsembleSize} (I_i + Q_i) \cdot (I_i - Q_i) \quad (1)$$

$$R(T) = \sum_{i=2}^{NewEnsembleSize} (I_i + Q_i) \cdot (I_{i-1} - Q_{i-1}) \quad (2)$$

Here, as in the example, NewEnsembleSize=3, T=1/PRF'=0.6 ms. Then the flow velocity, flow variance and flow energy can be calculated as:

$$v = \frac{\text{angle}(R(T)) \cdot PRF'}{2\pi f_0} \cdot \frac{c}{2\cos\theta} \quad (3)$$

$$\text{var} = PRF'^2 \cdot \left(1 - \frac{|R(T)|}{R(0)}\right) \quad (4)$$

$$e = R(0) \quad (5)$$

where c is the sound propagation velocity in tissue, and $f_0$ is the transmit center frequency, θ is the angle between ultrasound beam and flow direction. Three sets of velocity, variance and energy estimation, set 1, $(v_1, \text{var}_1, e_1)$, set 2, $(v_2, \text{var}_2, e_2)$, set 3, $(v_3, \text{var}_3, e_3)$ can be acquired from the three new sub-group ensemble sets at PRF. These three flow estimations are then averaged in 709 to get velocity estimation vL, variance estimation varL, and energy estimation eL:

$$vL=(v_1+v_2+v_3)/3; \quad (6)$$

$$\text{var}L=(\text{var}_1+\text{var}_2+\text{var}_3)/3; \quad (7)$$

$$eL=(e_1+e_2+e_3)/3. \quad (8)$$

If the imaging center frequency, fc, equals 3 MHz, this flow path provides a non-aliased flow estimation up to a maximum flow velocity of $vL=c*PRF/(3*4*f_0)=0.1283$ m/s, which is quite reasonable for general Abdomen, OB, and Renal clinical applications. Further, due to the three groups averaging effect, the SNRs of the estimated flow parameters are $\sqrt{3}$ times the SNRs of the parameters estimated from just one set of decimated data points since the noise are not correlated while flow signal are correlated. This yields a 4.8 dB SNR improvement, which largely compensates the 6 dB SNR loss in estimated flow parameters caused by the 3 times down sampling, and ends up only 1.2 dB SNR loss compared to an imaging sequence at PRF'=1.67 KHz with ensemble size equals 9. If the original ensemble size is 12 at PRF 5 KHz, and decimation ratio remains 3, the new ensemble size after down sampling will be 4 at PRF'=1.67 KHz, and 3 sub-groups ensemble data with PRF'=1.67 KHz can be used for averaging. In this case, the SNR loss in flow estimation is dropped to 0.9 dB.

In this method, the original high PRF can always be calculated based on the desired frame rate, desired ensemble size and number of beams as:

$$PRF = \text{beam} \times \text{ensembleSize} \times FR \qquad (9).$$

Here, beam is the number of beam positions in the color flow region of interest, FR is the frame rate. The desired PRF' can always be acquired by down sampling the acquired IQ data with an integer number decimation ratio.

Figure 10:
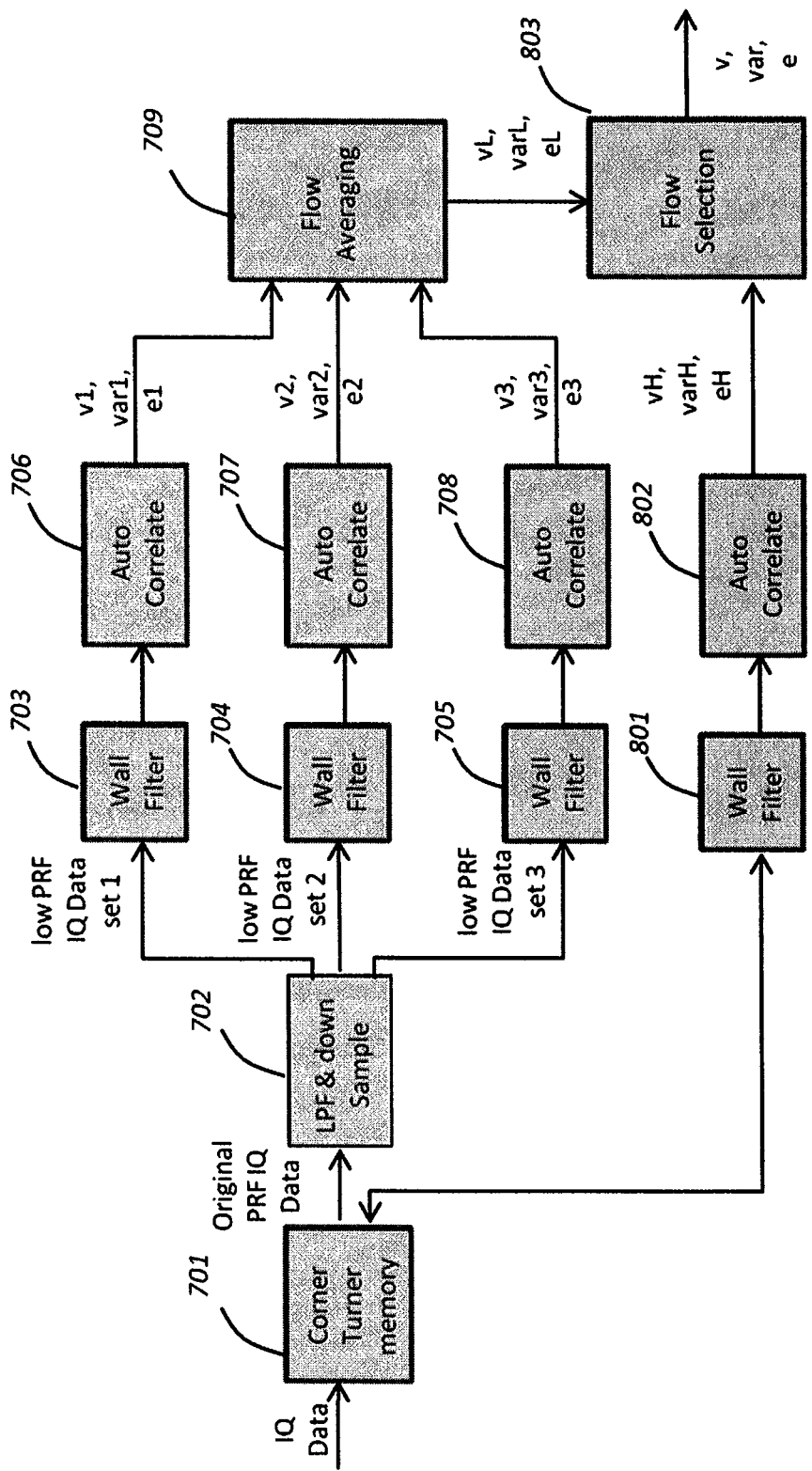
FIG. 10 is a configuration block diagram of one embodiment of the multi-path color flow processing for a system with a mechanically scanned ultrasound transducer in accordance with an embodiment of the disclosed technology.

Method 2: The above described method can be further improved by introducing a two path color flow processing scheme. In the two paths processing scheme, beyond the above described multi-group down-sampled color flow estimation as path 1, the system also processes the IQ data at original PRF 5 KHz in a second path 2, as shown in 801, 802 of FIG. 10. In this path, the original PRF IQ data is sent to wall filter 801, and auto correlate 802 to get direct flow estimations vH, varH and eH, using equation (3), (4), (5) though the 1.67 KHz PRF' is changed to original 5 KHz PRF. If the imaging center frequency, fc, equals 3 MHz, this flow path provides a non-aliased flow estimation up to a maximum flow velocity of $v=c*PRF/(4*f_0)=0.6417$ m/s, which is quite fast. Path 2 is thus a fast flow estimation path.

Flow estimations from path 1 and path 2 data are sent to the flow selection functional block 803 where a flow selection scheme is applied to determine the final flow parameter velocity—v, variance—var, and energy—e. One of such flow selection scheme is illustrated here:
 1) If vH>vL_max, here vL_max=c*PRF/(decimation_ratio*4*fc), then v=vH, var=varH, e=eH;
 2) Otherwise, v, var, and e will equal to the set of flow estimations from one of the paths in which the energy estimation e is greater than the energy estimation from another path.

This flow selection scheme guarantees non-aliased flow estimation up to a fairly high velocity while in the same time provides good slow flow estimation through multi-sub group low PRF flow processing.

Modifications of the first method and the second method based on many known techniques in color flow imaging are possible. For example, the wall filter in 703, 704, 705, 801 can be an adaptive wall filter where clutter will be detected first to determine the cutoff frequency for the wall filter. Further, the wall filter in 703, 704, 705 and 801 can be different.

With careful selection of light materials and large scale integrated electronic circuits, the weight of the overall system plus the mechanical scan transducer assembly can be held to under four pounds.

Figure 11:
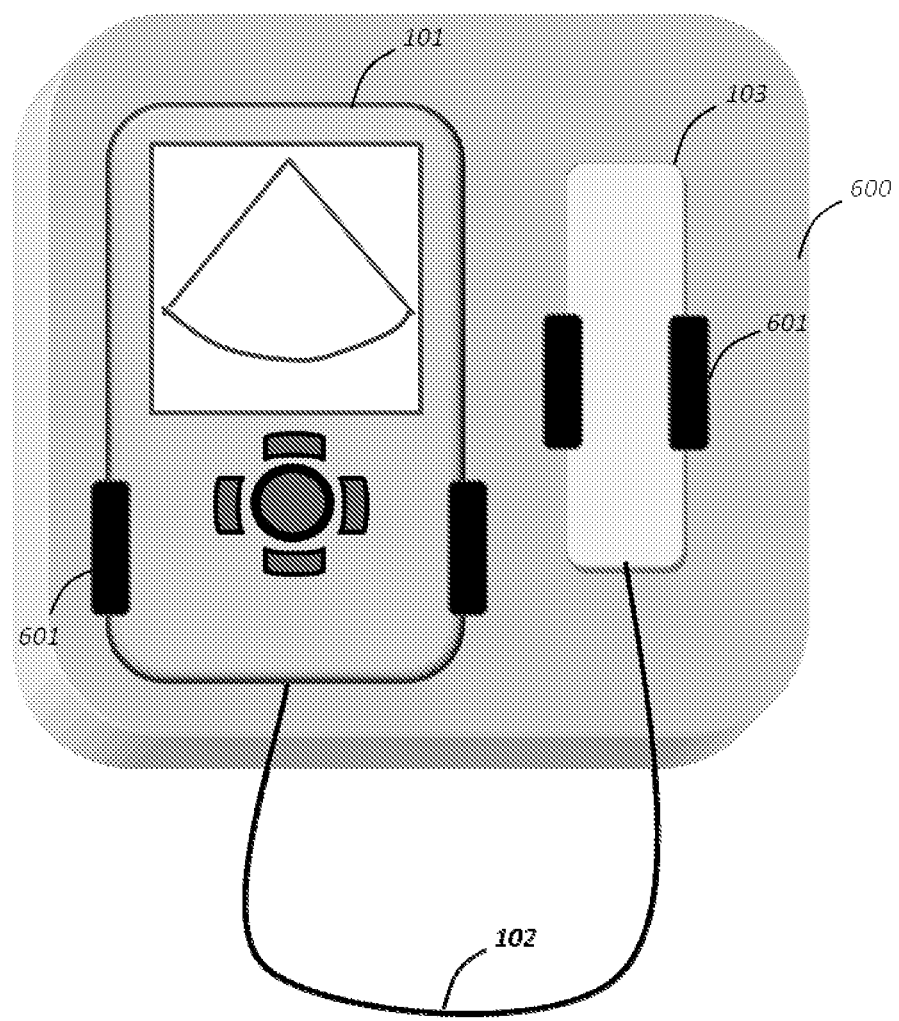
FIG. 11 illustrates one embodiment of a multi-function intelligent battery charging dock.

In one embodiment, the invention also includes a multi-function intelligent battery charging dock. Dock 600, shown in FIG. 11, can be mounted on a wall, IV pole or put on a flat surface. The portable imaging system 101 sits on the dock, secured by mechanical holder 601. A customized interface on the back of the portable imaging system connects the system with the dock. Transducer assembly 102 is attached to the dock through mechanical holder 601.

Figure 12:
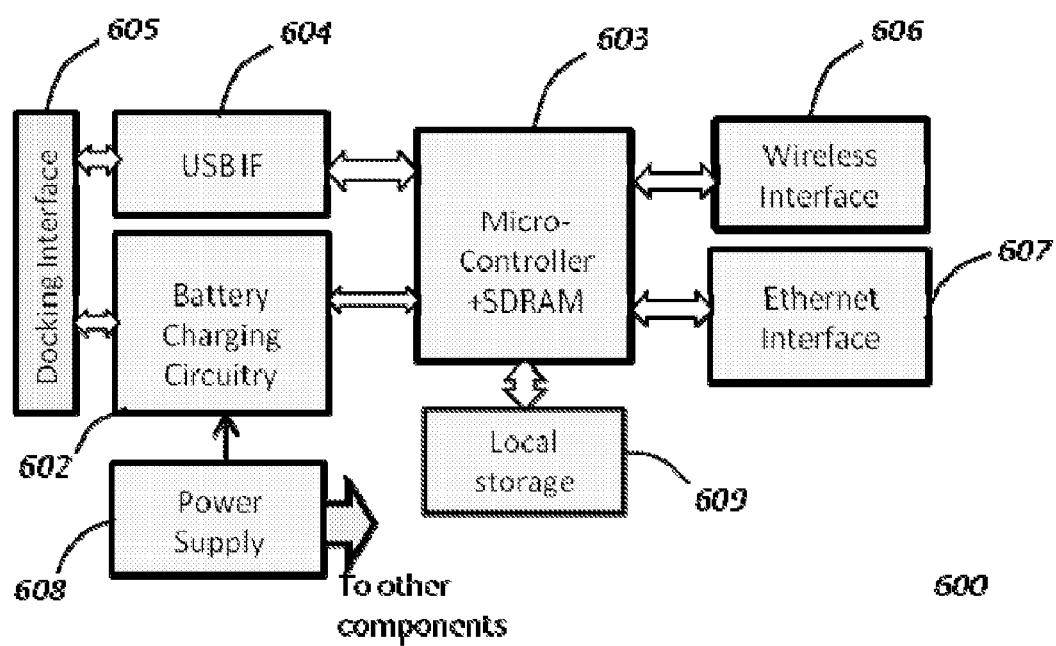
FIG. 12 is a configuration block diagram of the docking system.

FIG. 12 represents the block diagram of the docking system 600. The dock includes a battery charging circuit 602 which charges the system battery from fully discharged to 85% charge in 1 hour or less. The dock also includes a micro-controller and SDRAM unit 603 which controls the charging scheme, and the image data transfer from the portable imaging system to a workstation, PACS system or other system in either raw data or DICOM format. The micro-controller has a DICOM encoder which combines the images stored in the handheld with patient data and transfers them in DICOM format, or it can be programmed to transfer the image data and patient data into any other format that the hospital PACS system requires. The micro-controller 603 also allows for transferring of patient management data from a workstation or hospital information system to the portable imaging system for handling information such as patient identification, patient images, lab data or other types of data. The micro-controller 603 communicates with the portable imaging system through a USB2.0 interface 604 or other type of high speed interface. The USB 2.0 interface 604 is combined with charging power lines to form a customized docking interface 605 between the portable imaging system and the dock. The communication between micro-controller 603 and an outside workstation or PACS system is either through Ethernet interface 606, or through wireless connection interface 607, or through a direct USB2.0 interface. A power supply unit 608 supplies power to the battery charge circuit and other components in the dock.

The portable imaging system usually sits in the dock when not used for scanning The patient information is sent to the portable system through the dock or the user can use the portable imaging system sitting in the dock as a touch screen to input patient information. The micro-controller 603 then sends the patient information to a workstation or PACS system. The user removes the portable imaging system from the dock for patient scanning After the user finishes scanning with portable imaging system 101 and places it back in the dock 600, a predefined communication protocol will setup communication between the dock and the portable imaging system. If newly stored images or clips are found on the portable imaging system, the micro-controller in the dock downloads these images and clips into local storage 609 and sends them to a workstation or PACS system after combining this information with corresponding patient information. Local storage can be a flash driver or a hard disk driver. A predefined battery charging protocol running on the micro-controller 603 will check imaging system battery capacity and start the charging process. The micro-controller in the dock is also responsible for upgrading portable imaging system software if a new version is available.

Although the embodiment of the ultrasound imaging system as presented has been detailed, certain changes may be possible and these changes should not depart from the scope of this invention. For example, a large scale DSP processor may be used to do all the mid processing and backend processing. The docking system may also be used for image processing, such as speckle reduction of the received B mode images. Further, instead of multi-element annular array, the transducer can also be a single element circular transducer for B-mode and color flow imaging or other imaging modes. All such modifications and variations are intended to be included within the scope of the invention as defined in the claims that follow.

While illustrative embodiments have been illustrated and described, it will be appreciated that various changes can be made therein without departing from the scope of the invention.

The embodiments of the invention in which an exclusive property or privilege is claimed are defined as follows:

1. A portable ultrasound imaging system, comprising:
   an ultrasound transducer configured to direct acoustic ultrasound signals into a body and produce corresponding electronic echo signals therefrom;
   a mechanical mechanism configured to orient the ultrasound transducer in a desired direction;
   a transmitter configured to control production of the acoustic ultrasound signals from the ultrasound transducer;
   a receiver configured to receive the electronic echo signals from the ultrasound transducer and to process and digitize the electronic echo signals; and
   a processor configured to control the mechanical mechanism for orienting the ultrasound transducer and to produce image data for gray scale B-mode tissue images from the digitized echo signals,
   wherein the processor is further configured to produce image data for color flow images from the digitized echo signals by:
   (a) controlling the mechanical mechanism such that the ultrasound transducer is oriented in a desired direction;
   (b) controlling the transmitter to produce a number of acoustic ultrasound signals that are delivered into a body in the desired direction at a first pulse repetition frequency (PRF);
   (c) receiving digitized echo signals for a number of ensemble beams created in response to the number of acoustic ultrasound signals delivered;
   (d) selecting data from all of the ensemble beams at a desired depth to produce a set of digitized echo signals at the first PRF;
   (e) regrouping the set of data at the first PRF to produce new sets of digitized echo signals, each with data obtained at a second PRF by selecting data from fewer than all the ensemble beams;
   (f) calculating flow parameters from the data in each new set of digitized echo signals;
   (g) combining the flow parameters calculated from the new sets of digitized echo signals to produce the flow data for the desired depth;
   (h) shifting to another depth and repeating steps (d)-(g) until all desired depths along the beam in the desired direction are finished;
   (i) moving the transducer to a new desired direction and repeating steps (a)-(h) to get a flow estimation at all desired depths at the new desired direction; and
   (j) repeating steps (a)-(i) until a whole flow region of interest is covered,
   wherein the processor controls the mechanical mechanism such that the data for each of the number of ensemble beams in the desired direction is obtained before the ultrasound transducer is oriented in a new direction.

2. The portable ultrasound imaging system of claim 1, wherein the second PRF is lower than the first PRF.

3. The portable ultrasound imaging system of claim 1, wherein the processor is configured to combine the flow parameters calculated from the new sets of digitized echo signals by averaging the flow parameters calculated from the new sets of digitized echo signals.

4. The portable ultrasound imaging system of claim 1, wherein the processor is configured to calculate flow data from digitized echo signals selected from all the ensemble beams at the first PRF in addition to calculating flow parameters from the digitized echo signals at the second PRF in the new sets of digitized echo signals.

5. The portable ultrasound imaging system of claim 4, wherein the processor is further configured to calculate the flow data for the desired depth by:
   determining if a flow velocity estimation calculated from the digitized echo signals at the first PRF is greater than a maximum flow velocity that can be estimated from the digitized echo signals at the second PRF, and if so selecting the flow data determined from the digitized echo signals at the first PRF to be the flow data for the desired depth; otherwise selecting as the flow data for the desired depth the flow data calculated from the digitized echo signals at the first or second PRF that has a higher estimated flow power.

6. The portable ultrasound imaging system of claim 1, wherein the ultrasound transducer is a multi-element annular array transducer having two or more elements, wherein each of the two or more elements is mechanically focused at a depth different than the other elements.

7. The portable ultrasound imaging system of claim 6, wherein each of the two or more elements has a lens and is focused at a depth different than the other elements, and wherein the lenses for the two or more elements are different in shape and thickness.

8. The portable ultrasound imaging system of claim 6, wherein each of the two or more elements has an acoustic stack, and wherein each of the two or more elements is focused at a depth different than the other elements by having a different radius of curvature on the acoustic stack.

9. The portable ultrasound imaging system of claim 6, wherein the processor is configured to:
   (a) selectively turn on different elements of the multi-element annular array for transmitting acoustic signals into tissue in accordance with a depth of a received echo signal; and
   (b) selectively combine digitized electronic echo signals produced by different elements of the multi-element annular array in accordance with a depth of a received echo signal.

10. The portable ultrasound imaging system of claim 1, wherein the ultrasound transducer is a single element circular transducer focused at a fixed depth either through a lens or through application of a fixed radius of curvature on an acoustic stack.

11. The portable ultrasound imaging system of claim 1, wherein the mechanical mechanism is a motor coupled to the ultrasound transducer to change an angular orientation of the ultrasound transducer.

12. The portable ultrasound imaging system of claim 1, wherein the mechanical mechanism is a motor and a track, wherein the ultrasound transducer is movably mounted on the track and the motor is configured to move the ultrasound transducer on the track.

13. The portable ultrasound imaging system of claim 1, wherein the mechanical mechanism is a linear or curve linear motor, wherein a fixed part of the motor is a straight or curve linear rail with coils buried inside, and a moving part of the motor is a cart that is configured to move along the rail, the moving part and the fixed part together forming the linear or curve linear motor, and wherein the ultrasound transducer is mounted on the moving cart of the linear or curve linear motor and is configured to move along the rail when the linear or curve linear motor is operating.

14. The portable ultrasound imaging system of claim 1, wherein the processor is configured to produce data for M-mode imaging, pulse wave Doppler imaging, and continuous wave Doppler imaging from the digitized echo signals.

15. The portable ultrasound imaging system of claim 1, wherein the ultrasound imaging system weighs less than four pounds.

16. The portable ultrasound imaging system of claim 1, further comprising a docking station including:
- a battery charging circuit;
- a micro-controller and SDRAM unit that controls the battery charging circuit and that communicates with the portable imaging system and one or more remote health care information systems;
- a local storage unit that stores data; and
- a serial port interface to communicate with the portable ultrasound imaging system.

17. The portable ultrasound imaging system of claim 1, wherein the flow parameters include at least one or more of velocity, variance, and energy, and wherein calculating the flow parameters from the digitized echo data involves at least one or more of wall filtering, auto correlation, and flow estimation.

* * * * *